United States Patent [19]

Merianos et al.

[11] Patent Number: 5,158,768

[45] Date of Patent: Oct. 27, 1992

[54] PROCESS FOR PREPARING A STABLE, LOW K-VALUE, WATER-SOLUBLE PVP-IODINE PRODUCT

[75] Inventors: John J. Merianos, Middletown; Paul Garelick, South Plainfield, both of N.J.

[73] Assignee: ISP Investments Inc., Wilmington, Del.

[21] Appl. No.: 773,169

[22] Filed: Oct. 8, 1991

[51] Int. Cl.$^5$ ................... A61K 31/74; A61K 33/36
[52] U.S. Cl. ................... 424/78.36; 424/667
[58] Field of Search ............... 424/78.36, 667

[56] References Cited

PUBLICATIONS

World Patent Index 001582432. (Feb. 16, 1976).

*Primary Examiner*—Frederick E. Waddell
*Assistant Examiner*—Zohreh A. Fay
*Attorney, Agent, or Firm*—Walter Katz; Marilyn J. Maue; Joshua J. Ward

[57] ABSTRACT

A method of preparing a stable, low K-value, water-soluble polyvinylpyrrolidone-iodine product in the form of a uniform, free-flowing powder which comprises mixing a given amount of water-soluble polyvinylpyrrolidone polymer having a K-value of about 10-20 and about 10-20% by wt. iodine, and about 0.1-0.5% isopropanol, intimately mixing the reactants at room temperature for a sufficient period of time for the iodine to disappear as a separate phase, and then heating the reaction powders while mixing at about 65°-85° C. for a reaction period of at least about 18 hours.

11 Claims, No Drawings

PROCESS FOR PREPARING A STABLE, LOW K-VALUE, WATER-SOLUBLE PVP-IODINE PRODUCT

BACKGROUND OF THE INVENTION

1. Field of the Invention

This invention relates to a process for preparing polyvinylpyrrolidone-iodine (PVP-$I_2$), and, more particularly, to a method of making a stable, low K-value, water-soluble PVP-$I_2$ in the form of a uniform, free-flowing powder.

2. Description of the Prior Art

The reaction product of PVP with elemental iodine, known as PVP-iodine, or PVP-$I_2$, is marketed as a brown powder which contains about 11% of available iodine, i.e. active iodine, which can be titrated with sodium thiosulfate, and, in addition, contains about 5.5% of iodine in the form of iodide. At an iodine:iodide ratio of 2:1, the iodine bonding in the PVP-iodine complex is so strong that an iodine odor is no longer perceptible and a moist potassium iodide/starch paper introduced into the gas space above the PVP-iodine no longer acquires a color. In practice, the measure employed to assess whether the iodine is sufficiently firmly bonded is the partition coefficient of the iodine between an aqueous PVP-iodine solution and heptane, and this coefficient, as described, for example, in U.S. Pat. No. 3,028,300, should be about 200. Further it is necessary that in its formulations, in particular in aqueous solution, the PVP-iodine should lose very little available iodine on storage, i.e. it should be very stable.

Very diverse measures have been described for the preparation of a stable PVP-iodine. For example, according to German Pat. No. 1,037,075, the pulverulent PVP-iodine was subjected to a lengthy heat after-treatment at 90°–100° C.; while U.S. Pat. No. 2,900,305 proposed using a PVP having a defined moisture content for the preparation of a suitable PVP-iodine. U.S. Pat. No. 2,826,532 disclosed the addition of sodium bicarbonate; and U.S. Pat. No. 3,028,300 the addition of iodide in the form of hydrogen iodide or of an alkali metal iodide. U.S. Pat. No. 3,898,326 proposed the addition of hydrogen iodide or of an alkali metal iodide to an aqueous PVP solution, followed by reaction of the pulverulent PVP-iodide mixture, obtained from the solution after drying, with iodine. German Published Application DAS 2,439,197 stated that polyvinylpyrrolidone polymerized in an anhydrous organic solvent was particularly suitable for the preparation of a stable PVP-iodine.

The above prior art processes are also intended to permit economical preparation of a stable PVP-iodine. However, they also suffer from substantial disadvantages. According to the process described in German Pat. No. 1,037,075, for example, heating for from 18 to 64 hours at 90°–100° C. to form the PVP-iodine complex was necessary to obtain a stable product having an iodine:iodide ratio of 2:1. The process described in U.S. Pat. No. 2,900,305 entailed heating PVP and iodine for 22 hours at 90°–100° C.

According to U.S. Pat. No. 3,028,300, heating can be dispensed with if iodide in the form of an alkali metal iodide or hydriodic acid is added to the mixture of polyvinylpyrrolidone and iodine. This process, however, does not represent an optimum, since inhomogeneous mixtures are formed, in which the iodine is only weakly bonded, and, accordingly a strong smell of iodine is present. A related process without heat treatment was proposed in U.S. Pat. No. 3,898,326 wherein iodides, e.g. as HI or NaI, were added to an aqueous polyvinylpyrrolidone solution, drying, and the pulverulent polyvinylpyrrolidone/iodide mixture reacted with iodine. However, HI causes corrosion problems on drying, while NaI increase the alkali content above the stringent requirements of the drug laws. German Published Application DAS 2,439,197 suggested a heating time of 10 hours; however to achieve a partition coefficients of about 200 it was necessary to heat for at least 20 hours.

The heating times can be greatly reduced, as disclosed in German Published Application DAS 2,818,767, PVP is reacted with elementary iodine in the presence of formic or oxalic acids, or an ammonium salt or amide of carbonic acid, formic acid or oxalic acid.

U.S. Pat. No. 4,402,937 described the preparation of the product in water rather than the solid state. The process comprised reacting PVP with elemental iodine in the presence of formic acid, oxalic acid or an ammonium salt or amide of carbonic acid, formic acid or oxalic acid, in aqueous solution.

These and other methods, however, have not provided a process for making stable, PVP-iodine complexes having a K-value of about 10–20 which are water-soluble, uniform, free-flowing powders. Accordingly, it is the object of the present invention to provide a process for the preparation of such product.

These and other objects and features of the invention will become apparent from the following description.

SUMMARY OF THE INVENTION

What is provided herein is a method of preparing a stable, low K-value, water-soluble polyvinylpyrrolidone-iodine complex in the form of a uniform, free-flowing powder. The process of the invention comprises mixing a given amount of a water-soluble, polyvinylpyrrolidone polymer having a K-value of about 10–20, about 10–20% by wt. iodine, about 0.1–1% isopropanol, intimately mixing the reactants at room temperature for a sufficient period of time for the iodine to disappear as a separate phase, and heating the reaction powder while mixing at about 65–85° C. for a reaction period of at least about 18 hours.

DETAILED DESCRIPTION OF THE INVENTION

The polyvinylpyrrolidone employed usually has a K value of from 10 to 20, the range from 13 to 17 being preferred. A polyvinylpyrrolidone which is particularly suitable for the process according to the invention is prepared by polymerization in an organic solvent, such as isopropanol or toluene, or a water-isopropanol mixture using an organic per-compound, e.g. a dialkyl peroxide, as a source of free radicals, with or without a subsequent steam distillation, as described, for example, in German Laid-Open Application DOS 2,515,127.

Polyvinylpyrrolidones which are subjected to a hydrogenation treatment after polymerization are also eminently suitable for the preparation of the stable PVP-iodine product of the invention. Such hydrogenation may be carried out in accordance with conventional processes, for example, by treatment of PVP with hydrogen in the presence of a suitable catalyst or by treatment with a complex hydride. Advantageously, the hydrogenation is carried out in aqueous solution at 20° to 100° C., preferably 50° to 80° C., under a pressure of from 50 to 500 bar, preferably from 200 to 300 bar, for 1 to 24 hours, as described in U.S. Pat. No. 2,914,516. Suitable catalysts are platinum, palladium and Raney nickel These and other suitable water-soluble PVP starting materials having a K-value of 10-20 may be obtained commercially from the International Specialty Products Inc. or BASF.

The product of the invention is prepared by reacting 80-90% by wt. PVP with 10-20% by wt. iodine at a temperature of about 65°-85° C., preferably about 75° C., for a period of at least about 18 hours, and, in the presence of a small amount, e.g. 0.1-0.2, preferably, 0.2%, of isopropanol.

The parameters of the process of the invention, and the product produced thereby are summarized in the Table below

TABLE

| Reaction Mixture and | Ranges | | |
|---|---|---|---|
| Process Conditions | Suitable | Preferred | Optimum |
| PVP (K = 10-20) | 80-90 | 81-85 | 83 |
| $I_2$ (% by wt.) | 10-20 | 15-19 | 17 |
| Isopropanol (% by wt.) | 0.05-1 | 0.1-0.5 | 0.2 |
| Room Temperature Mixing (hrs.) | 3-16 | 5-10 | 7.5 |
| Reaction Temp (°C.) | 65-85 | 70-80 | 75 |
| Reaction Time (hrs.) at least | 12 | >16 | 16-22 |
| Reaction Product | | | |
| K-Value | 10-20 | 13-17 | 15 |
| Avail $I_2$ (% by wt.) | 9-13 | 10.5-11.5 | 11 |
| Iodide (% by wt.) | 4-6 | 4.5-5.5 | 5 |
| Partition Coefficient | >150 | 180-220 | 200 |

The invention will now be described with reference to the following working Example.

EXAMPLE 60 g. of PVP (K-value 12-20) powder, 12.0 g. of iodine powder and 0.144 g. of isopropanol were mixed in a jar and the mixture was rotated with a motor driven rotary cage at 40 rpm at room temperature for 3-16 hours. The iodine powders disappeared as a separate phase and the reaction mixture was a uniform, nearly black powder which was flowable. This mixture then was rotated continuously at 75° C. for 22 hours. The product was a uniform, free-flowing, reddish-brown powder. The available iodine content was 10.99%, the iodide content was 4.80%; and the moisture content was 3.14%.

Stability was measured by % iodine loss after 6 hours at 75° C. from a 1% available iodine solution, only 3.64% of available iodine was lost. The partition coefficient of the product was 148.

While the invention has been described with particular reference to certain embodiments thereof, it will be understood that changes and modifications may be made which are within the skill of the art. Accordingly, it is intended to be bound only by the following claims, in which:

What is claimed is:

1. A method of preparing a stable, low K-value, water-soluble polyvinylpyrrolidone-iodine product in the form of a uniform, free-flowing powder which comprises mixing a given amount of a water-soluble polyvinylpyrrolidone polymer having a K-value of about 10 to about 20, about 10 to about 20% by wt. iodine, and 0.1 to about 1% by wt. isopropanol, intimately mixing the reactants at room temperature for a sufficient period of time for the iodine reactant to disappear as a separate phase, and heating the reaction mixture while mixing at a reaction temperature of about 65° to about 85° C. for a reaction period of at least about 18 hours.

2. A method according to claim 1 wherein said reaction temperature is about 70-80° C.

3. A method according to claim 1 wherein about 15-19% by wt. iodine is present in the reaction mixture.

4. A method according to claim 1 wherein about 0.1-0.5% by wt. isopropanol is included in the reaction mixture.

5. A method according to claim 1 wherein the amount of available iodine in the product is about 9-13%, and the iodide content is about 4-6%.

6. A method according to claim 1 wherein the partition coefficient of the product is at least about 150.

7. A method according to claim 1 wherein the reaction powders are mixed at room temperature for about 3-16 hours.

8. A method according to claim 1 wherein the K-value of the product is about 13-17.

9. A method according to claim 1 wherein the reaction period is about 18-22 hours.

10. A method according to claim 1 wherein the available iodine in the product is about 10.5-11.5% by wt., the iodide content is about 4.5-5.5% by wt., and its partition coefficient is about 180-220.

11. A method according to claim 1 wherein, in the reaction mixture, the amount of iodine is about 17% by wt., the amount of isopropanol is about 0.2%, the reaction temperature is about 75° C., and the reaction time is about 18-22 hours, and the product has a K-value of about 15, the available iodine therein is about 11% by wt., and the iodide content is about 5% by wt.

* * * * *